(12) United States Patent
Harms et al.

(10) Patent No.: US 9,381,305 B2
(45) Date of Patent: Jul. 5, 2016

(54) MEDICAL DEVICE

(75) Inventors: Michael Harms, Frankfurt am Main (DE); Steffen Raab, Frankfurt am Main (DE); Udo Stauder, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 434 days.

(21) Appl. No.: 13/258,162

(22) PCT Filed: Mar. 31, 2010

(86) PCT No.: PCT/EP2010/054345
§ 371 (c)(1),
(2), (4) Date: Dec. 30, 2011

(87) PCT Pub. No.: WO2010/112561
PCT Pub. Date: Oct. 7, 2010

(65) Prior Publication Data
US 2012/0109075 A1    May 3, 2012

Related U.S. Application Data

(60) Provisional application No. 61/169,865, filed on Apr. 16, 2009.

(30) Foreign Application Priority Data

Mar. 31, 2009 (EP) .................................. 09004668

(51) Int. Cl.
*A61M 5/315* (2006.01)
*A61M 5/31* (2006.01)
(52) U.S. Cl.
CPC .......... *A61M 5/31525* (2013.01); *A61M 5/315* (2013.01); *A61M 5/31543* (2013.01); *A61M 2005/3115* (2013.01)

(58) Field of Classification Search
CPC ............ A61M 5/20; A61M 2005/202; A61M 2005/2026; A61M 5/24; A61M 5/28; A61M 2005/2403; A61M 5/2033; A61M 5/3159; A61M 5/31591; A61M 5/31543; A61M 5/31525; A61M 5/31528; A61M 5/3158; A61M 5/315; A61M 5/31546; A61M 5/3155
USPC .................................. 604/208, 211, 224, 506
See application file for complete search history.

(56) References Cited

U.S. PATENT DOCUMENTS 4,694,946 A    9/1987 Pearch et al.
5,505,704 A *  4/1996 Pawelka .................. A61M 5/19
                                              604/191

(Continued)

FOREIGN PATENT DOCUMENTS

| EP | 1704883 | 9/2006 |
|---|---|---|
| EP | 1704884 | 9/2006 |
| JP | 2002-242969 | 8/2002 |
| JP | 2008-057692 | 3/2008 |
| WO | 94/22507 | 10/1994 |

OTHER PUBLICATIONS

Smalley Steel Ring Company—http://www.smalley.com/wave_springs/Crest-to-Crest.asp—Feb. 11, 2009.*

(Continued)

*Primary Examiner* — Emily Schmidt
*Assistant Examiner* — William Frehe
(74) *Attorney, Agent, or Firm* — McDonnell Boehnen Hulbert & Berghoff LLP (57) ABSTRACT

The medical device comprises a wave spring or wave washer in a mechanism to engage or disengage a first element and a second element. The invention also discloses the use of a multiple wave spring or wave washer comprising at least two waved spring layers in a medical device.

12 Claims, 4 Drawing Sheets

(56) References Cited

U.S. PATENT DOCUMENTS

| | | | | |
|---|---|---|---|---|
| 5,593,390 | A | * | 1/1997 | Castellano .......... G06F 19/3468 128/DIG. 1 |
| 7,169,128 | B2 | * | 1/2007 | Kriesel ................. A61M 5/141 604/133 |
| 7,220,245 | B2 | | 5/2007 | Kriesel |
| 7,462,169 | B2 | | 12/2008 | Follman et al. |
| 2004/0210199 | A1 | | 10/2004 | Atterbury et al. |
| 2005/0277882 | A1 | | 12/2005 | Kriesel |
| 2007/0093761 | A1 | * | 4/2007 | Veasey .............. A61M 5/31546 604/207 |

OTHER PUBLICATIONS

Smalley Steel Ring Company http://www.smalley.com/waye_springs/Crest-to-Crest.asp, Feb. 11, 2009 web page.*
European Search Report for EP Patent Application No. 09004668, dated Aug. 17, 2009.
International Search Report for PCT Patent Application No. PCT/EP2010/054345, dated Jul. 13, 2010.
International Preliminary Report on Patentability for International App. No. PCT/EP2010/054345, dated Oct. 4, 2011.

* cited by examiner

MEDICAL DEVICE

CROSS REFERENCE TO RELATED APPLICATIONS

The present application is a U.S. National Phase Application pursuant to 35 U.S.C. §371 of International Application No. PCT/EP2010/054345 filed Mar. 31, 2010, which claims priority to European Patent Application No. 09004668.1 filed on Mar. 31, 2009 and U.S. Provisional Patent Application No. 61/169,865 filed on Apr. 16, 2009. The entire disclosure contents of these applications are herewith incorporated by reference into the present application.

FIELD OF INVENTION

This invention relates to the use of a wave spring or wave washer in a medical device, especially a drug delivery device or injection device.

BACKGROUND

The application of mechanisms in medical devices is accompanied with an increasing demand for mechanical components or elements that require only a restricted volume. This is true especially of portable medical devices that are used by patients and have to be everywhere available. If a mechanism of restricted dimensions requires the application of a spring force, the operation of the mechanism is essentially affected by the properties of the spring element. Therefore, a number of different spring types are used in medical devices or have been suggested for an application in conjunction with medical devices, especially with injection or infusion devices.

U.S. Pat. No. 7,462,169 B2 discloses a safety shield system for an injection pen needle. A mechanically operating part of the injection pen needle can be equipped with a wave spring. U.S. Pat. No. 7,220,245 B2 discloses an infusion apparatus, which is furnished with a flow control means, for which, inter alia, the use of wave springs is recommended.

EP 1 704 883 B1 and EP 1 704 884 B1 disclose devices for administering a fluid product in doses. An embodiment comprises a cylindrical drive member having a thread inside and an output member as well as an adjustment element both having a screw thread of the same pitch. A spring is arranged between the drive member and the adjustment element in order to enhance the friction between the threads. The drive member and the adjustment element can have structures inhibiting a rotation of the adjustment element within the drive member. A further embodiment comprises a screw-like drive member and a wave spring arranged between the housing and a transfer element, which is in contact with a drive ring of the drive member. The transfer element can be rotationally fixed with respect to the housing. The transfer element and the drive ring preferably form a pair of sliding faces.

SUMMARY

It is an object of the present invention to disclose a means of providing medical devices having mechanically operating components with sufficiently strong spring force elements of restricted dimensions.

This object is achieved with the medical device according to claim 1 and with the use of a wave spring or wave washer according to claim 12, respectively. Further aspects and variations of the invention derive from the depending claims.

The medical device according to the invention comprises a mechanism having a first element and a second element, which are engaged by a coupling device, and a spring arranged in contact with at least one of the elements and tending to engage or disengage the first element and the second element. The spring can especially be arranged between the first element and the second element and tend to disengage the elements. If the spring disengages the first element and the second element, the elements can be moved relatively to one another. The spring is selected to be a wave spring or wave washer, preferably a multiple wave washer having a plurality of waved spring layers of an elastic material, especially a metal, mounted sequentially one above another.

The medical device can especially be a drug delivery device or an injection device, particularly in the shape of a pen. Since such an injection pen is designed to be handy and everywhere available, the mechanism provided for the operation of the injection device has to be arranged within very restricted dimensions. It is therefore important to have the necessary spring force be provided by a spring element that occupies as little volume as possible. Using a wave spring or wave washer allows to enhance the effective spring force while restricting the occupied volume essentially. This is not easily achieved with conventional spring elements. It is a further advantage of a wave spring or wave washer to have a relatively large spring constant so that a large spring force is generated by a relatively small compression of the spring. The dimensions of the spring can therefore be kept small. The plurality of elevated contact areas formed on the waved outermost spring layers render an improved homogeneity of the distribution of the spring force over the areas where the spring force is applied, as compared to a helical spring. The application of wave springs or wave washers within medical devices is especially favorable if the spring is formed of a plurality of waved layers in the shape of an annular multiple wave washer.

BRIEF DESCRIPTION OF THE FIGURES

Further aspects and examples of the invention are described in conjunction with the appended figures of which

DETAILED DESCRIPTION

Figure 1:
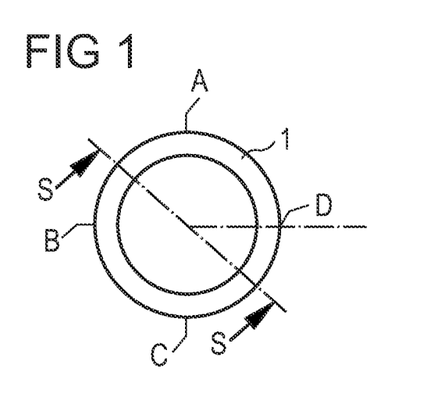
FIG. 1 shows a plan view onto an annular wave washer.
Figure 2A:
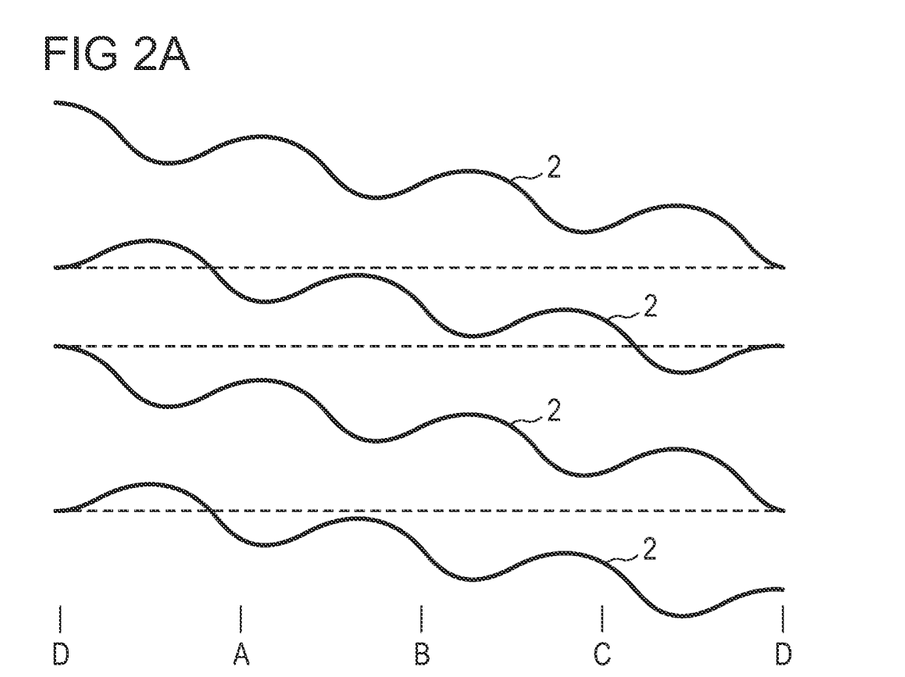
FIG. 2A shows a lateral view of a wave spring.
Figure 2B:
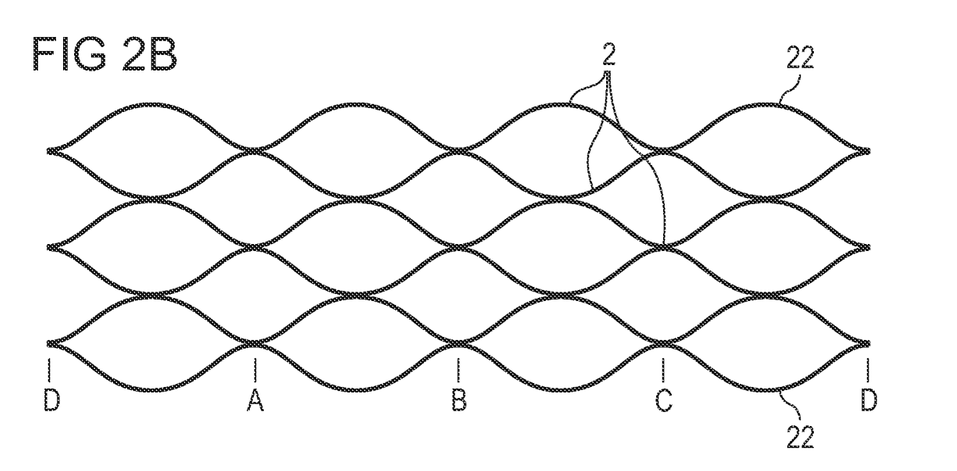
FIG. 2B shows a lateral view of a multiple wave washer.

FIGS. 1, 2A and 2B serve to explain the shape of a typical multiple wave spring or wave washer that is especially suitable for an application in a medical device. FIG. 1 shows a plan view onto a helical wave spring or wave washer, which appears in the shape of an annulus 1 in this perspective. FIG. 2A shows a lateral view of a helical wave spring according to FIG. 1, the circumference of the wave spring having been unwound after a severance at point D, so that the lateral area of the cylindrical volume encompassed by the wave spring is projected into the plane of the drawing. Letters A to D are inserted as marks of reference between FIGS. 1 and 2A and show the relative positions of locations of the turns 2 of the wave spring. The wave spring can be formed in one piece by a curved wire or band comprising waves in the direction in which the spring force is to be exerted, for example. This amounts to a helical spring having bows in axial direction.

The broken lines in FIG. 2A indicate how the wire or band of the wave spring continues at point D. The waves of the wave spring can have a sinusoidal shape, for example. When being free of tension or stress, the spring layers 2 can be narrower than shown in FIG. 2A. The outermost turns of the wire can be formed to be essentially, besides the waves, parallel to a plane that is perpendicular to the axis of the wire helix, similar to the outermost spring layers 22 of the further example shown in FIG. 2B. This is especially suitable, because the most elevated areas of the outer surfaces of the outermost spring layers thus formed can easily be brought into contact with a flat surface on which the spring force or pressure is to be exerted, and the spring force is distributed rather homogeneously over the surface.

FIG. 2B shows a lateral view according to FIG. 2A of a further example of a wave spring or wave washer, which is made up of several spring layers 2. Letters A to D are inserted as marks of reference between FIGS. 1 and 2B and show the relative positions of locations of the waved spring layers 2. The wave spring of FIG. 2B is formed of at least two waved spring layers 2 of an elastic material mounted one above the other and making several contacts with the preceding and subsequent spring layers 2, respectively. The outermost spring layers 22 can be formed to be essentially, besides the waves, parallel to a plane that is perpendicular to the axis of the wave washer, as shown in FIG. 2B.

In one general aspect, the invention discloses the use of a wave spring or wave washer comprising at least two waved turns or waved spring layers in a medical device. The wave spring or wave washer is especially suitable for a use in a medical device of restricted dimensions, if there is a plurality of waved turns 2 or spring layers as shown in FIGS. 2A and 2B, where the number of waved turns 2 or spring layers is four and six, respectively. The elastic material of which the wave spring or wave washer is manufactured can be a metal. The wave spring can be formed by a waved wire helix, or waved spring layers 2 can be mounted sequentially one above another. The waved shape of the spring layers 2 renders a good distribution of the spring force all over the annulus 1, shown in FIG. 1, which defines the area in which the spring force is exerted.

Figure 3:
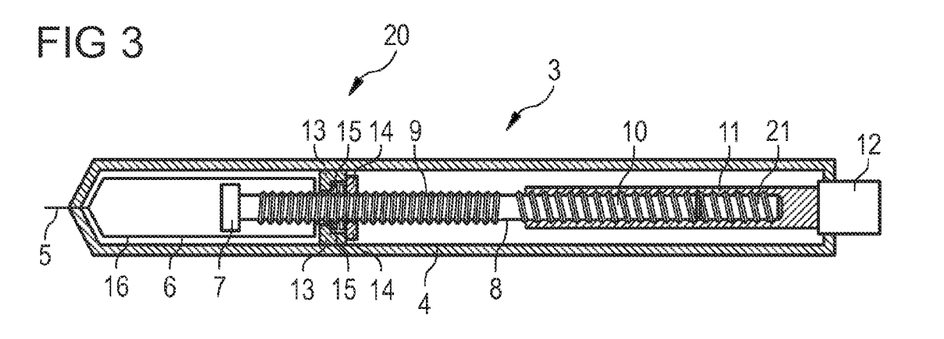
FIG. 3 shows a cross-section of an injection pen.

FIG. 3 shows an embodiment of a medical device comprising a mechanism that is equipped with a wave spring or wave washer. The medical device of this embodiment is a pen-type drug delivery device or injection pen. Such a device is used to inject a prescribed dose of a pharmaceutical substance or fluid from a reservoir within the device, which is emptied in correspondence with the applied doses. FIG. 3 shows a cross-section of an injection pen 3 encompassing a mechanism 20 comprising a wave spring or wave washer as spring force element. The mechanism 20 is shown as an example of the essential part of the medical device according to the invention. A further mechanism which can be provided to enable the setting of a dosage is not shown in detail and can be realized in various embodiments within the scope of the invention.

The injection pen 3 shown in FIG. 3 comprises a body 4, which is in the shape of a pen and is supplied with a needle 5 at one end, designated by distal end in the following, and an operation button 12 at the opposite end, designated by proximal end in the following. A receptacle 6 is provided for the reception of a substance or fluid that is to be delivered or injected through the needle 5. Instead of being filled directly into the receptacle 6, the substance or fluid can be introduced into the receptacle 6 by means of a cartridge 16. Refilling the injection pen is thus simplified. A piston 7 is arranged in the receptacle 6 either for reuse or for exchange together with the cartridge 16, and is moved in the longitudinal direction of the injection pen 3 by means of a piston rod 8. The piston rod 8 is moved in the longitudinal direction by means of the operation button 12 and further mechanical components which are not shown in detail.

The substance or fluid in the receptacle 6 or cartridge 16 can e.g. be a medicament.

The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39), des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence

H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-desAsp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In the embodiment shown in FIG. 3, the piston rod 8 is realized in the form of a so-called leadscrew comprising a first screw thread 9 located on a section of the piston rod 8 near the piston 7 and a second screw thread 10 located on a further section of the piston rod 8 at a larger distance from the piston 7. The second screw thread 10 can be engaged with a corresponding thread 21 of the same pitch on the inner surface of an operation sleeve 11, for example. The operation sleeve 11 can be used together with further mechanical components not shown in FIG. 3 to provide a mechanism that is used for setting a dosage, which enables to move the piston rod 8 and the piston 7 by prescribed intervals along the longitudinal extension of the piston rod 8. In a reusable device, the mechanism can additionally serve to reset the piston rod 8 to a starting position so that the receptacle 6 can be refilled or the cartridge 16 exchanged. The mechanism 20 which is of primary interest in connection with the present invention is described in the following in more detail.

The mechanism 20 shown in FIG. 3 comprises a first element 13, which is a lock nut in this embodiment, a second element 14, which is a piston rod nut in this embodiment, and a spring 15 arranged between the first element 13 and the second element 14. A coupling device is provided for engaging the first element 13 and the second element 14 and can be realized, for instance, by interlocking teeth on opposing surfaces of the elements. When the injection pen 3 is ready for use, the spring 15 is compressed, and the coupling device engages the first element 13 and the second element 14. The compressed spring tends to disengage the first element 13 and the second element 14. In the example shown in FIG. 3, the compression of the spring 15 is effected by the cartridge 16 inserted in the receptacle 6. Therefore, the lock nut 13 and the piston rod nut 14 are engaged when the injection pen 3 is used.

Figure 4:
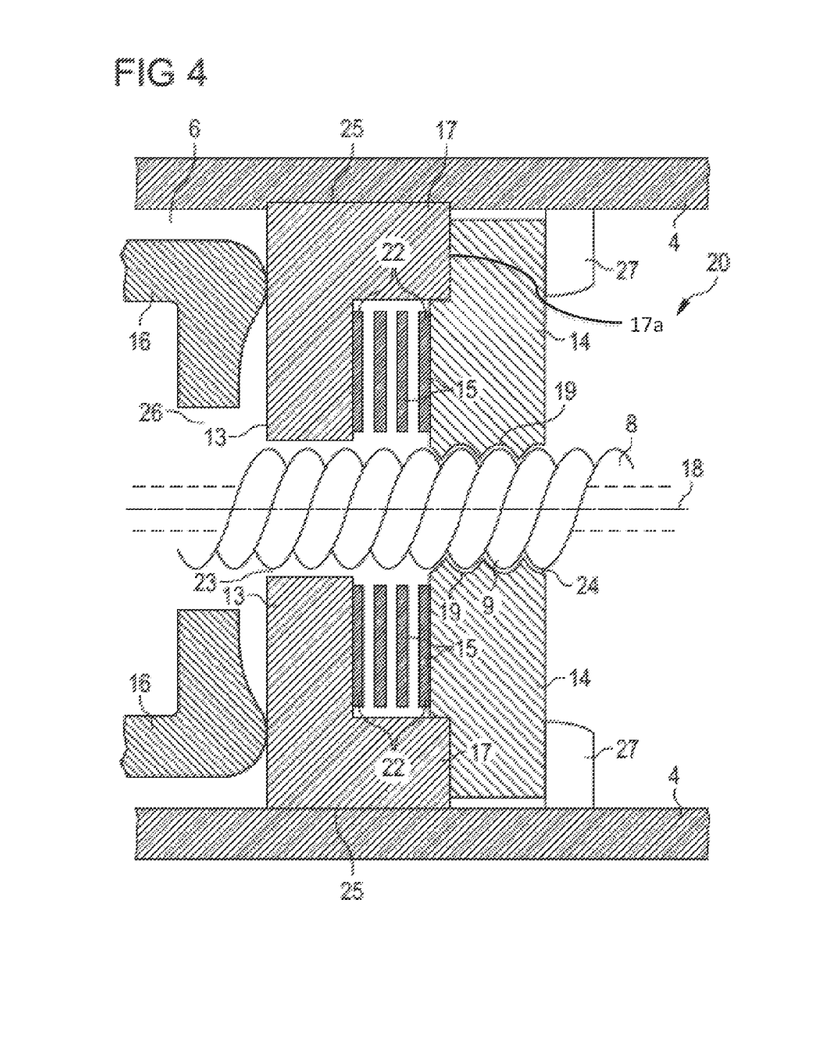
FIG. 4 shows an enlarged cross-section of a mechanism of the injection pen according to FIG. 3.

FIG. 4 shows the mechanism 20 in an enlarged view with more details. In the center of FIG. 4, a section of the piston rod 8 is shown. An imaginary central axis 18 is indicated by the broken line of alternating dots and dashes. The piston rod 8 goes through a hole 23 of the lock nut 13, a hole 24 of the piston rod nut 14 and a hole 26 in the bottom of the cartridge 16, which is inserted in the receptacle 6. The spring 15 is situated between the lock nut 13 and the piston rod nut 14, and its spring layers are shown as thin metal layers as viewed in the direction of the cross-section indicated with S in FIG. 1. The spring 15 surrounds the piston rod 8 in the annular shape of a washer. The raised or embossed portions of the outer surfaces of the outermost spring layers 22 are in contact with the surfaces of the lock nut 13 and the piston rod nut 14 facing the spring 15. This is shown in the cross-section of FIG. 4, which represents the spring 15 at locations in which the outer surfaces of the outermost spring layers 22 are most elevated and in contact with the nuts 13, 14. These are the locations of the wave spring in the middle between the positions marked A, B, C, D in FIG. 2B, for example.

The coupling device 17 engaging the lock nut 13 and the piston rod nut 14 can be formed by a sequence of interlocking teeth 17a or some other kind of gear, for example. This is indicated in FIG. 4 by the lock nut 13 partially intruding the outer margin of the piston rod nut 14 with the interlocking teeth 17a in the area of the coupling device 17. The lock nut 13 is engaged with the body 4, by means of protruding parts or recesses 25, for example, so that the lock nut 13 cannot rotate relatively to the body 4 around the axis 18 of the piston rod 8. A translational motion of the lock nut 13 in the direction towards the piston 7 can be inhibited by the presence of the cartridge 16. The movement of the nuts 13, 14 in the opposite direction away from the piston 7 can be inhibited by barrier rims 27 or spikes, for example, which are fixed at the inner surface of the body 4 on the side of the nuts 13, 14 facing away from the piston 7.

The hole 24 of the piston rod nut 14 is supplied with a thread 19 having the same pitch as the piston rod screw thread 9. Thus, the thread 19 of the piston rod nut 14 is the female thread counterpart of the male screw thread of the piston rod 8. If the nuts are engaged by the coupling device 17 as shown in FIG. 4, a relative rotation of the lock nut 13 and the piston rod nut 14 is inhibited, and the piston rod nut 14 cannot rotate relatively to the body around the piston rod 8 because the lock nut 13 is rotationally fixed by the recesses 25.

If the cartridge 16 is removed and the spring 15 is released, the coupling device 17 is no longer interlocked, and the lock nut 13 and the piston rod nut 14 are disengaged. This means that the piston rod nut 14 can freely rotate around the piston rod 8, and the piston rod 8 is able to perform a translational movement along its axis 18 irrespective of a rotation around its axis 18. This is, because the piston rod nut 14 will freely rotate and compensate for a discrepancy between the actual translational movement of the piston rod 8 and a translational component of a helical movement of the piston rod 8 generated by the threads 9, 19 when the piston rod nut 14 is rotationally fixed. In particular, after the piston rod nut 14 having been released, the piston rod 8 need not rotate at all when it is shifted along its axis 18 in the direction away from the piston 7. In the latter case a relative rotation of the piston rod 8 with respect to the piston rod nut 14 caused by the treads 9, 19 is effected by only the piston rod nut 14 rotating relatively to the body 4. This feature may be of advantage for resetting the piston rod 8 to a starting position suitable for refilling the injection pen. The reset can be performed by shifting the piston rod 8 back to a starting position without having to care about an appropriate rotational movement of the piston rod 8.

The described injection pen is only one embodiment of the medical device according to this invention, which shows by way of example the improvements and advantages that are obtained by the use of a wave spring or wave washer in medical devices, especially a multiple wave washer comprising a plurality of spring layers, particularly in view of obtaining a relatively strong and better distributed force or pressure within reduced dimensions.

The invention claimed is:

1. A medical device comprising: a dose delivery mechanism comprising a piston rod, the piston rod having a screw thread being located a first distance near a piston and a further screw thread located at a second distance from the piston, where the second distance is greater than the first distance and the piston rod rotates during dose delivery; a lock nut and a piston rod nut of the mechanism, where one of the lock nut or the piston rod nut is threadedly engaged with the piston rod; a coupling device configured to cause the lock nut and the piston rod nut to engage each other to prevent relative rotation between them; a spring arranged in contact with at least one of the lock nut and the piston rod nut and tending to engage or disengage the lock nut and the piston rod nut; and the spring being a wave spring or wave washer.

2. The medical device according to claim 1, further comprising: a body; a receptacle in the body; a piston movable in the receptacle by means of a piston rod having an axis; the piston rod going through holes in the lock nut and the piston rod nut of the mechanism; the lock nut being engaged with the body in such a manner as to inhibit a rotation of the lock nut relatively to the body around the axis of the piston rod; the piston rod nut being engaged with the piston rod in such a manner as to generate an axial rotation of the piston rod relatively to the piston rod nut when the piston rod is moved along its axis relatively to the piston rod nut; the coupling device engaging the lock nut and the piston rod nut in such a manner as to inhibit a rotation of the piston rod nut relatively to the lock nut around the axis of the piston rod; and the spring being arranged between the lock nut and the piston rod nut and tending to disengage the lock nut and the piston rod nut.

3. The medical device according to claim 2, further comprising: the receptacle being provided for a cartridge; the lock nut and the piston rod nut of the mechanism being engaged when a cartridge is in the receptacle; and the spring disengaging the lock nut and the piston rod nut when no cartridge is in the receptacle.

4. The medical device according to claim 3 where the cartridge contains a medicament.

5. The medical device according to claim 4, wherein the medicament is a pharmaceutical formulation containing at least one pharmaceutically active compound which comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

6. The medical device according to claim 2, wherein the lock nut and the piston rod nut of the mechanism are disengaged by means of the spring when the piston rod is reset or moved to a starting position.

7. The medical device according to claim 1, further comprising:
a cylindrical operation sleeve surrounding the piston rod; and
the operation sleeve having a thread engaging the further screw thread of the piston rod.

8. The medical device according to claim 7, wherein the screw thread of the piston rod has a smaller pitch than the further screw thread.

9. The medical device according to claim 1, wherein the spring is formed by a helically curved wire comprising waves in the direction in which the spring force is to be exerted.

10. The medical device according to claim 1, wherein the spring is formed of at least two waved layers of an elastic material mounted one above the other.

11. The medical device according to claim 1, wherein the coupling device is formed by surface structures comprising interlocking teeth on opposing surfaces of the nuts.

12. The medical device according to claim 1, wherein the device is a pen-type drug delivery device or injection device.

* * * * *